US008709738B2

(12) United States Patent
Bacus

(10) Patent No.: US 8,709,738 B2
(45) Date of Patent: Apr. 29, 2014

(54) METHODS FOR PREDICTING CARDIAC TOXICITY

(75) Inventor: Sarah S. Bacus, Hinsdale, IL (US)

(73) Assignee: Quintiles Transnational Corporation, Durham, NC (US)

( * ) Notice: Subject to any disclaimer, the term of this patent is extended or adjusted under 35 U.S.C. 154(b) by 1222 days.

(21) Appl. No.: 12/280,893

(22) PCT Filed: Feb. 27, 2007

(86) PCT No.: PCT/US2007/062871
§ 371 (c)(1),
(2), (4) Date: Mar. 31, 2009

(87) PCT Pub. No.: WO2007/101191
PCT Pub. Date: Sep. 7, 2007

(65) Prior Publication Data
US 2009/0186910 A1 Jul. 23, 2009

Related U.S. Application Data

(60) Provisional application No. 60/867,736, filed on Nov. 29, 2006, provisional application No. 60/828,345, filed on Oct. 5, 2006, provisional application No. 60/827,372, filed on Sep. 28, 2006, provisional application No. 60/821,230, filed on Aug. 2, 2006, provisional application No. 60/777,096, filed on Feb. 27, 2006.

(51) Int. Cl.
*C12Q 1/60* (2006.01)
*A01N 43/58* (2006.01)
*A61K 31/30* (2006.01)

(52) U.S. Cl.
USPC .......................................... 435/11; 514/247

(58) Field of Classification Search
None
See application file for complete search history.

(56) References Cited

U.S. PATENT DOCUMENTS

2005/0089899 A1    4/2005    Birnbaum et al.

FOREIGN PATENT DOCUMENTS

| WO | 03028271 | 4/2003 |
| WO | 2004042360 | 5/2004 |

OTHER PUBLICATIONS

Burris "Dual Kinase Inhibition in the Treatment of Breast Cancer: Initial Experience with the EGFR/ErbB-2 Inhibitor Lapatinib," (Abstract Only) The Oncologist Jun. 2004 vol. 9 Supplement 3, pp. 10-15.*

Kumar-Sinha et al., "Transcriptome Analysis of HER2 Reveals a Molecular Connection to Fatty Acid Synthesis", Cancer Res 2003;63:132-139.*
Dillman (Cancer Metastasis Rev. 1999;18(4):465-71).*
An et al., "The Metabolic Switch AMPK Regulates Cardiac Heparin-Releasable Lipoprotein Lipase," Am. J. Physiol. Endocrinol. Metab. vol. 288, pp. E246-E253 (2004).
Tokarska-Schlattner et al., "Acute Toxicity of Doxorubicin on Isolated Perfused Heart: Response of Kinases Regulating Engery Supply," Am. J. Physiol. Heart Circ. Physiol., vol. 289, pp. H37-H47 (2005).
An et al., "The metabolic switch AMPK regulates cardiac heparin-releasable lipoprotein lipase," Am. J. Physiol. Endocrinol. Metabl, Aug. 24, 2004, vol. 288, pp. E246-E253, especially abstract; p. E246.
European Search Report for European Publication No. 1996939, dated Mar. 12, 2009.
Feldman, Arthur M. et al., "Trastuzumab in the treatment of metastic breast cancer: Anticancer therapy versus cardiotoxicity," Circulation, vol. 102, No. 3, Jul. 18, 2000, pp. 272-274.
Grazette, L P et al., "Inhibition of ErbB2 causes mitochondrial dysfunction in cardiomyocytes Implications for herceptininduced cardiomyopathy," Journal of the American College of Cardiology, Elsevier, New York, NY, US, vol. 44, No. 11, Dec. 7, 2004, pp. 2231-2238.
Huss, Janice M. et al., "Mitochondrial energy metabolism in heart failure: a question of balance," Journal of Clinical Investigation, American Society for Clinical Investigation, US, vol. 115, No. 3, Mar. 1, 2005, pp. 547-555.
International Search Report for International Application No. PCT/US07/62871, dated Oct. 1, 2007.
Morandi, P. et al., "Cardiac toxicity of high-dose chemotherapy," Bone Marrow Transplantation Feb. 2005, vol. 35, No. 4, Feb. 2005, pp. 323-334.
Rosenblatt-Velin, N. et al.,"Postinfarction heart failure in rats is associated with upregulation of GLUT-1 and downregulation of genes of fatty acit metabolism," Cardiovascular Research, Oxford University Press, vol. 52, No. 3, 1 Dec. 1, 2001, pp. 407-416.
Schneider, Jay W. et al., "Cardiotoxicity in signal transduction therapeutics: ErbB2 antibodies and the heart," Serminars in Oncology, W.B. Saunders, vol. 28, No. 5, suppl 16, Oct. 1, 2001, pp. 18-26.
Schneider, Jay W. et al., "Trastuzumab cardiotoxicity: Speculations regarding pathophysiology and targets for further study," Seminars in Oncology, vol. 29, No. 3, suppl 11, Jun. 2002, pp. 22-28.
Slichenmyer, William J. et al., "Anticancer therapy targeting the ErbB family of receptor tyrosine kinases," Serminars in Oncology, vol. 28, No. 5, suppl 16, Oct. 2001, pp. 67-79.

(Continued)

*Primary Examiner* — James D Anderson
*Assistant Examiner* — William Lee
(74) *Attorney, Agent, or Firm* — K&L Gates LLP

(57) ABSTRACT

Methods are disclosed for determining whether organ toxicity, particularly cardiotoxicity, will occur in a patient selected for treatment with various kinase inhibitors, such as tyrosine kinase inhibitors, more particularly erbB inhibitors such as Herceptin. In addition, methods are disclosed for determining whether a potential drug is likely to produce a cardiotoxic effect. The methods involve analyzing lipid levels or the expression fatty acid oxidation enzymes, pAMP activated protein kinase, glucose uptake, to determine whether a fatty acid oxidation disorder is present. The identification of a fatty acid oxidation disorder can be used as a predictor of toxicity, especially cardiac toxicity, and as an indication that organ function should be carefully monitored if a drug such as a tyrosine kinase inhibitor is administered. Methods are also disclosed for protecting organs from metabolic stress and for the treatment of cells, such as adipocytes, to reduce their lipid content.

17 Claims, 10 Drawing Sheets

(56) References Cited

OTHER PUBLICATIONS

Spector, Neil L. et al., "Activation of AMP-activated protein kinase by human EGF receptor 2/EGF receptor tyrosine kinase inhibitor protects cardiac cells," Proceedings of the National Academy of Sciences of the United States of America, Jun. 19, 2007, vol. 104, No. 25, Jun. 19, 2007, pp. 10607-10612.

Tokarska-Schlattner et al., "Acute toxicity of doxorubicin on isolated perfused heart: response of kinases regulating energy supply," Am. J. Physiol. Heart Circ. Physiol., Mar. 11, 2005, vol. 289, pp. H37-H47, especially abstract; Fig. 9; p. H37-H38; p. H45.

Waddell, et al., "Medium-chain acyl-CoA dehydrogenase deficiency: Genotype-biochemical phenotype correlations," Molecular Genetics and Metabolism, Academic Press, San Diego, CA, US, vol. 87, No. 1, Jan. 1, 2006, pp. 32-39.

Fujita et al. 2011 Tetrahydrobioproterin (BH4) Activates AMPK and Suppresses Hepatic Gluconeogensis through ENOS-Dependent Pathway. American Diabetes Association 71st Scientific Sessions, Monday, Jun. 27, 2011: 12:00 PM - 2:00 PM Abstract No: 1697-P.

Kumar-Sinha et al. Transcriptome Analysis of HER2 Reveals a Molecular Connection to Fatty Acid Synthesis, Cancer Research 63, 132-139, Jan. 1, 2003.

Russell et al. 2004. AMP-activated protein kinase mediates ischemic glucose uptake and prevents postischemic cardiac dysfunction, apoptosis, and injury. J Clin Invest 114: 495-503.

Shibata et al. 2005. Adiponectin protects against myocardial ischemia-reperfusion injury through AMPK- and COX-2-dependent mechanisms. Nature Medicine 11, 1096-1103 (2005) Published online: Sep. 11, 2005 | doi: 10.1038/nm1295.

Yamashiro et al. 2002 Beneficial effect of tetrahydrobiopterin on ischemia-reperfusion injury in isolated perfused rat hearts. J Thorac Cardiovasc Surg. Oct. 2002; 124(4): 775-84.

\* cited by examiner

Figure 1. Genes regulated by Herceptin® treatment in Au565 cells

DNA Repair (Down-regulated)
- RAD51-interacting protein (PIR51)
- p53 target zinc finger protein (WIG1)
- Exonuclease I (EXO1)
- BRCA2
- RAD51
- RAD54

Cell Cycle & DNA Synthesis (Down-regulated)
- Cyclin A2
- Cyclin D1
- Cyclin E2
- CHK1
- Thymidine kinase 1 (TK1)
- Early growth response 1 (EGR1)
- CTP synthetase (CTPS)
- Thymidylate synthase (TS)

Apoptosis (Up-regulated)
- TNFR1
- TRAIL
- Forkhead box O3A (FOXO3A)

Apoptosis (Down-regulated)
- FLIP
- NF-κB inhibitor-like 2 (NFKBIL2)
- Connective tissue growth factor (CTGF)
- Mitogen-inducible gene 6 (MIG-6)

Ion Channels (Up-regulated)
- Protein containing an IQ calmodulin-binding domain
- Sodium channel voltage-gated type I (alpha subunit) (SCN1A)

Ion Channels (Down-regulated)
- Calcium/calmodulin-dependent serine protein kinase (CASK)
- Serine-threonine protein kinase 33 (STK33)
- Calcium-activated chloride channel 1
- A kinase anchor protein 5 (AKAP5)

Translation (Up-regulated)
- Similar to yeast BMs1p (40S biogenesis)

Translation (Down-regulated)
- Eukaryotic initiation factor 5A (EIF5A)

Fatty Acid Metabolism/Regulation (Up-Regulated)
- NKX2-5
- ACOX2
- AFP
- S100A9

Fatty Acid Metabolism/Regulation (Down-Regulated)
- EMD
- TEAD1
- KCNH2
- SOAT1
- PERC
- FABP1
- CRBPIV

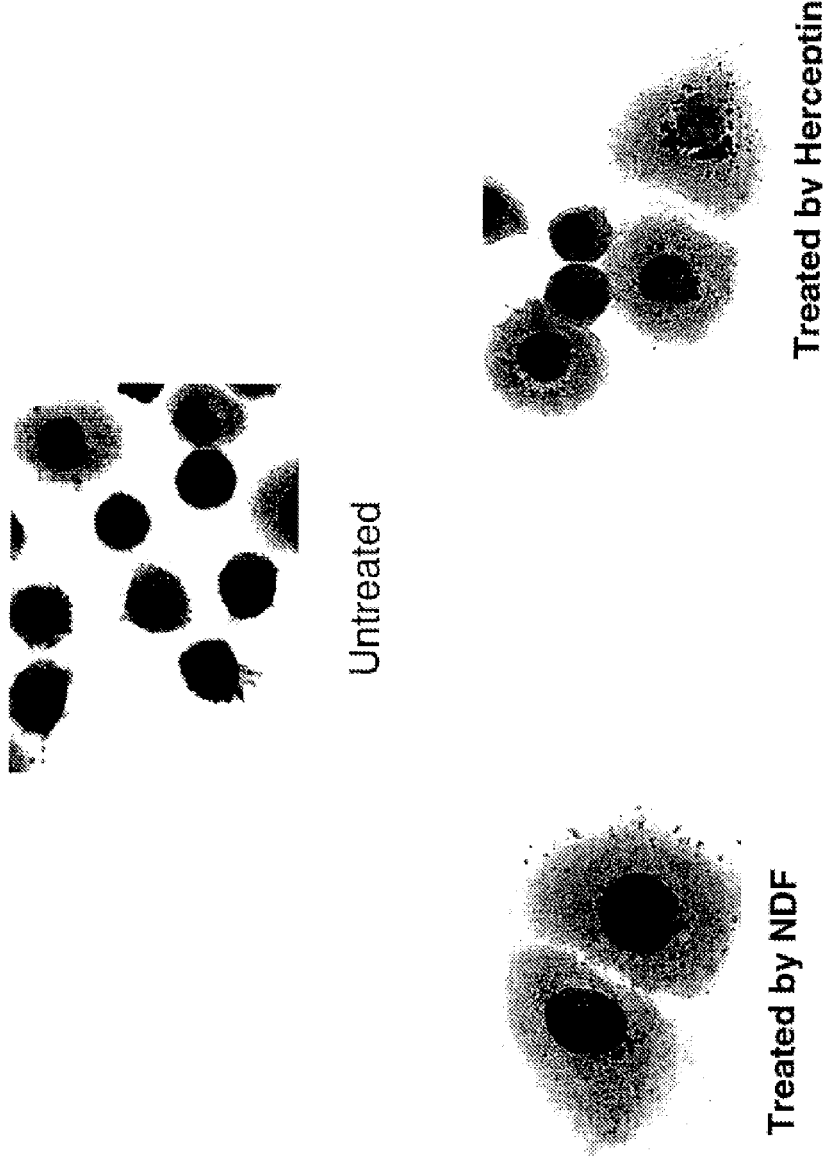

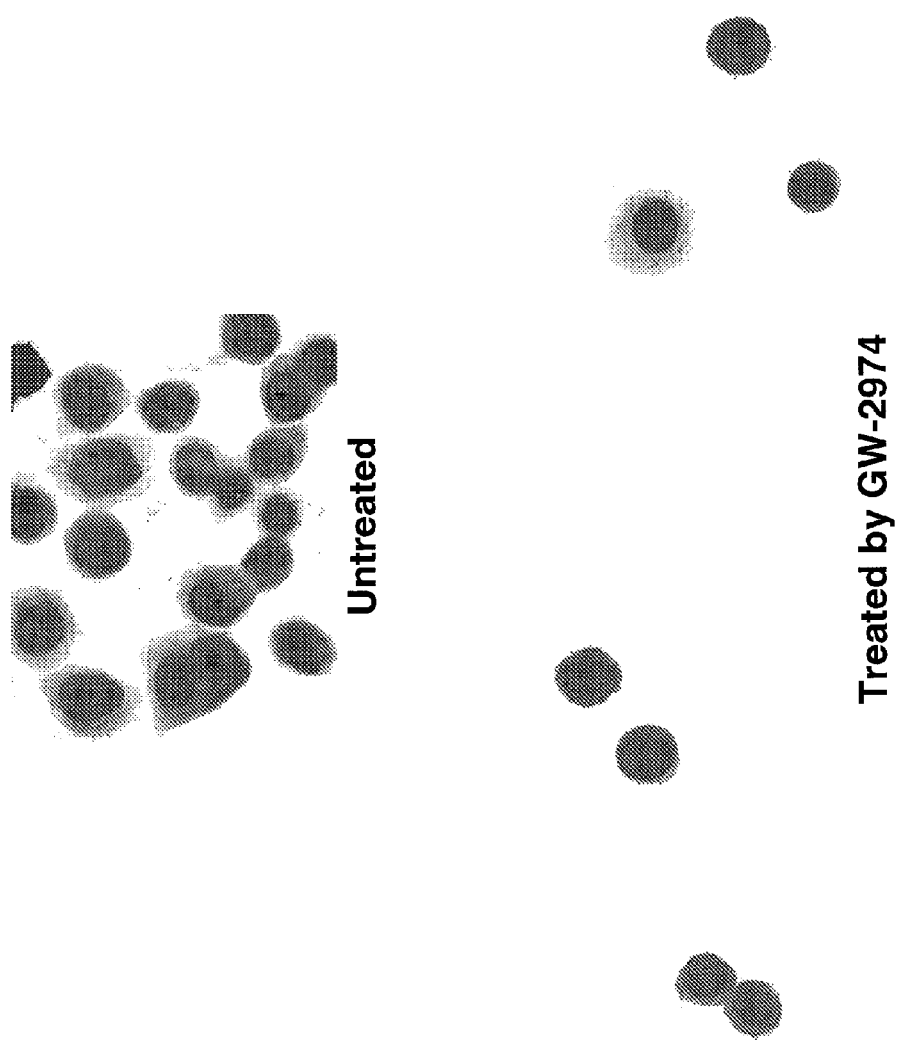

Figure 4. Primary Human Cardiac Myocytes and stained for lipids

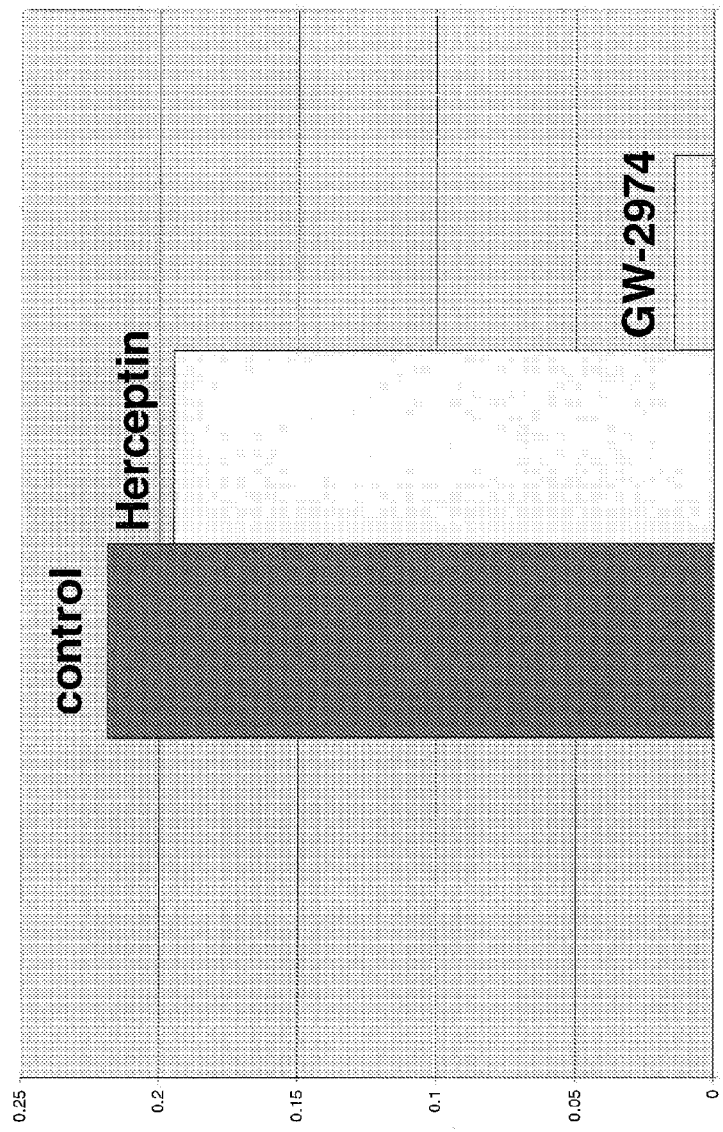
Figure 5. Human cardiomyocytes: % of cells positive for lipids

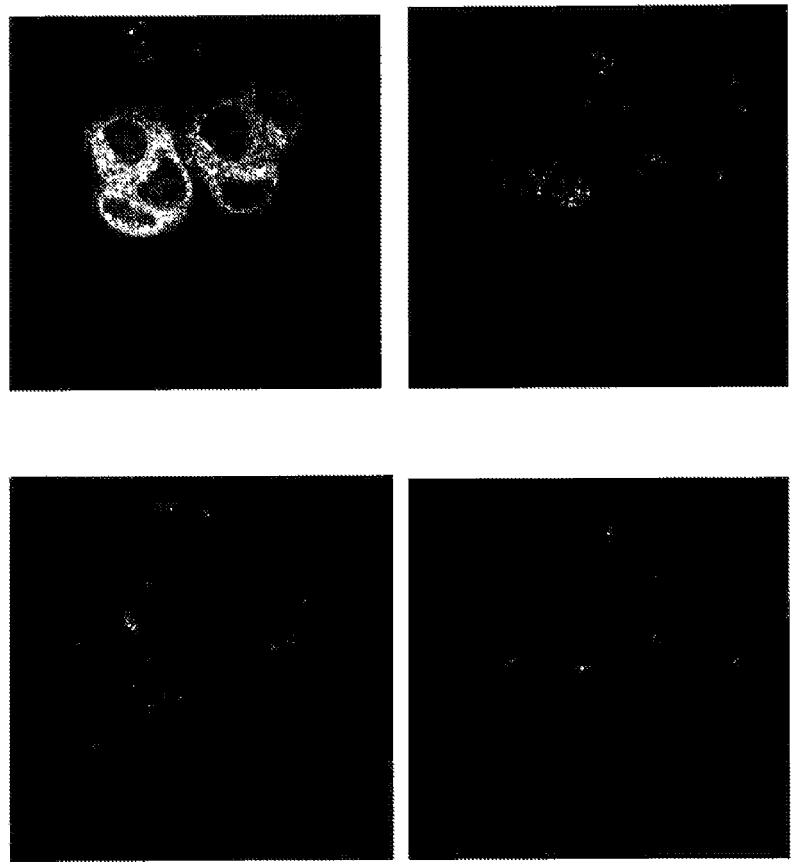
Figure 6. MDA-MB-468 cells treated by GW-2974 and intracellular Ca detected by Fluoro-4.

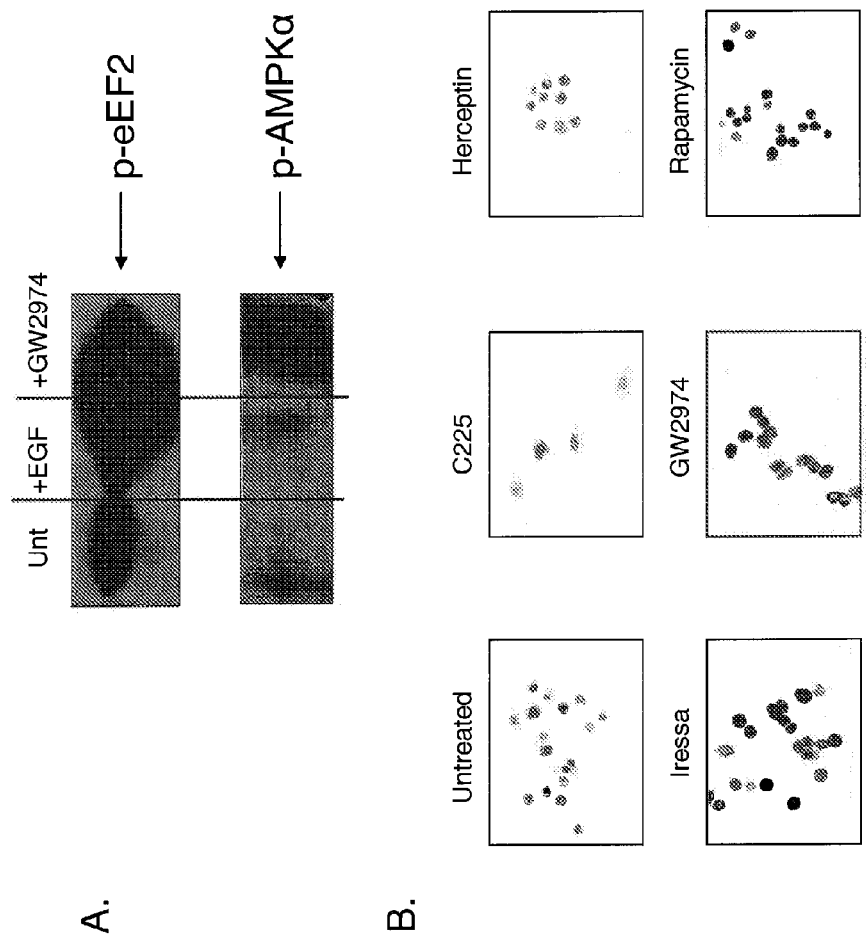
Figure 7. TKIs Are Involved In Regulation Of Translation

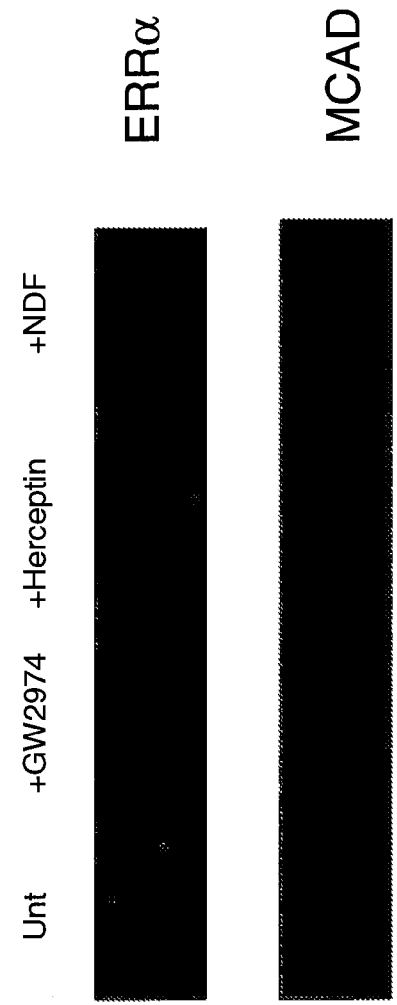
Figure 8. Expression of ERRα and MCAD in cardiomyocytes cells with and without treatment

METHODS FOR PREDICTING CARDIAC TOXICITY

PRIORITY CLAIM

This application claims priority to and the benefit of U.S. Patent Application Ser. No. 60/777,096, filed Feb. 27, 2006; U.S. Patent Application Ser. No. 60/821,230, filed Aug. 2, 2006; U.S. Patent Application Ser. No. 60/867,736, filed Nov. 29, 2006; U.S. Patent Application Ser. No. 60/828,345, filed Oct. 5, 2006; U.S. Patent Application Ser. No. 60/827,372, filed Sep. 28, 2006; and PCT Application Serial No. PCT/US2007/062871, filed Feb. 27, 2007.

BACKGROUND

The heart has a tremendous capacity for ATP generation which allows it to function as an efficient pump throughout the life of the organism. The adult myocardium uses either fatty acid (FA) and/or glucose oxidation as its main energy sources. Under normal conditions, the adult heart derives most of its energy through oxidation of fatty acids in mitochondria.

Cells of the myocardium have the ability to switch between carbohydrate glycolysis and the Krebs cycle and to fat fuel sources so that ATP production is maintained at a constant rate under diverse physiological and dietary conditions. This metabolic and fuel selection flexibility is important for normal cardiac function. Although cardiac energy conversion capacity and metabolic flux is modulated at many levels, one important mechanism of regulation occurs at the level of gene expression. The expression of genes involved in multiple energy transduction pathways is dynamically regulated in response to developmental, physiological, and pathophysiological cues.

The genes involved in these key energy metabolic pathways are transcriptionally regulated by members of the nuclear receptor superfamily, specifically the fatty acid-activated peroxisome proliferator-activated receptors (PPARs) and the nuclear receptor coactivator, PPARγ coactivator-1α (PGC-1α), as well as the estrogen receptor-related protein ERRα, ERRβ and ERRγ and their activators PGR-1 and PERC. The dynamic regulation of the cardiac PPAR/PGC-1 complex in accordance with physiological and pathophysiological states is described in more detail below.

PGC-1α is a PPARγ coactivator, linked to adaptive thermogenesis in brown adipose. Two structurally related proteins, PGC-1β and PARC, have been cloned and appear to be involved in regulating energy metabolic pathways. The tissue-specific and inducible nature of PGC-1α expression suggests its involvement in the dynamic regulation of cellular energy yielding metabolic processes, including mitochondrial biogenesis and oxidation, hepatic gluconeogenesis, and skeletal muscle glucose uptake. PGC-1α is selectively expressed in highly oxidative tissues such as heart, skeletal muscle, brown adipose, and liver. In the heart PGC-1α expression increases sharply at birth. This coincides with a perinatal shift from glucose metabolism to fat oxidation. PGC-1α activity and expression levels are also known to be induced by cold exposure, fasting, and exercise; stimuli known to promote oxidative metabolism. Forced expression of PGC-1 in cardiac myocytes in culture induces expression of nuclear and mitochondrial genes involved in multiple mitochondrial energy-transduction/energy-production pathways, increases cellular mitochondrial number, and stimulates coupled respiration. Signaling pathways associated with these stimuli, including p38 MAP kinase, β-adrenergic/cAMP, nitric oxide, AMP kinase, and $Ca^2$-calmodulin kinase, activate PGC-1α and its downstream target genes either by increasing PGC-1α expression or its transactivation function.

These metabolic and structural changes can result in dilated cardiomyopathy and diastolic dysfunction in the heart. Interestingly, mitochondrial proliferation is reversible and the cardiomyopathy can be rescued upon reduction in transgene expression. This suggests that, in addition to serving as an activator of cellular fatty acid metabolism through PPARs, PGC-1α is linked to the mitochondrial biogenesis. Therefore, PGC-1α appears to serve as a master modulator of oxidative energy metabolism and responds to changes in the cellular energy status.

Evidence is emerging that the estrogen-related receptor (ERR) family of orphan Nuclear Receptors function as PGC-1-activated regulators of cardiac and skeletal muscle energy metabolism. There are three members of the ERR family: ERRα, ERRβ, and ERRγ. ERRα and ERRγ expression is elevated in adult tissues that rely primarily on mitochondrial oxidative metabolism for ATP production, such as heart and slow twitch skeletal muscle. ERRα expression dramatically increases in heart after birth, in parallel with the global upregulation of enzymes involved in cellular fatty acid uptake and mitochondrial oxidation. Recently, ERRα and ERRγ were identified as novel partners for the PGC-1 family of coactivators. This functional relationship between ERR isoforms and PGC-1α have stimulated interest in the role of ERRs in energy metabolism.

Deletion of the ERRα gene reveals a tissue-specific role for ERRα in constitutive regulation of lipid metabolism. White adipose mass is decreased in ERRα-/- mice coincident with decreased adipocyte size and lipid synthesis rates. In contrast, ERRα likely plays a role in lipid catabolism in heart, consistent with its functional interaction with PGC-1α. ERRα-/- mice, which do not display an overt cardiac phenotype, exhibit a compensatory increase in cardiac PGC-1α and ERRγ expression. These results suggest that ERR isoforms contribute to constitutive expression of fatty acid metabolic genes in heart. However, the metabolic effects of changes in gene expression remain unknown.

Gene expression profiling in cardiac myocytes that overexpress ERRα are being used to identify cardiac ERRα target genes. ERRα activates genes involved in energy production pathways, including cellular fatty acid uptake (LPL, CD36/FAT, H-FABP, FACS-1), β-oxidation (MCAD, VLCAD, LCHAD), and mitochondrial electron transport/oxidative phosphorylation (cytochrome c, COXIV, COXVIII, NADH ubiquinone dehydrogenase, flavoprotein-ubiquinone oxidoreductase, ATP synthase β). ERRα also increases palmitate oxidation rates in cardiac myocytes. Activation of β-oxidation enzymes genes by ERRα involves the PPARα signaling pathway. ERRα directly activates PPARα gene expression, and ERRα-mediated regulation of MCAD and M-CPT I is abolished in cells derived from PPARα-/- mice. ERRα is also now known to be involved in the PGC-1α regulation of mitochondrial biogenesis. It is known to mediate PGC-1α activation of the NRF pathway through regulation of the Gapba gene, which encodes a subunit of the NRF-2 complex and directly activates genes involved in mitochondrial oxidative metabolism at the level of transcription. ERRα with its coactivator PGC-1α activates the MCAD, cytochrome c, and ATP synthase β gene promoters. Collectively, these results identify ERRα as a regulator of cardiac oxidative energy metabolism through its involvement in the PGC-1 regulatory circuit. However, the precise biological roles of ERRs in heart have not been identified.

The nuclear receptor ERRγ (estrogen related receptor gamma) is highly expressed in heart, skeletal muscle, kidney, and brain, as well as in the developing nervous system. The expression of the coactivators PGC-1α and PGC-1β in mammalian cells potently augmented transcriptional activation by ERRγ. The constitutive activation function 2 (AF-2) of the orphan receptor is important for the synergistic enhancement. Functional receptor truncation analysis has been used to identify an additional amino-terminal activation function, specific for the ERRγ2 isoform and PGC-1α. In vitro experiments showed a direct interaction of ERRγ with both coactivators. These findings are consistent with the hypothesis that distinct regulatory functions for PGC-1α and PGC-1β as tissue-specific coactivators for ERRγ. Nevertheless, more studies are needed to further define these functions.

Cardiac-specific overexpression of PGC-1 in transgenic mice results in uncontrolled mitochondrial proliferation in cardiac myocytes leading to loss of sarcomeric structure and a dilated cardiomyopathy. Thus, PGC-1 is an important regulatory molecule in the control of cardiac mitochondrial number and function in response to energy demands.

Most, if not all of these regulatory pathways involve phosphorylation of intermediates in a signaling pathway. Inhibition of phosphorylation, such as by the action of various kinase inhibitors, affects these signaling pathways causing alterations in fatty acid metabolism which can cause organ toxicity, including cardiotoxicity. Many new anti-cancer drugs are kinase inhibitors and are accompanied by toxicity. Thus, methods are needed for identifying whether drugs may be accompanied by toxic effects and whether the toxic effects are likely to occur in a patient. Methods are also needed for avoiding toxic effects of these inhibitors while maintaining their potency against the phosphorylated receptor targets.

SUMMARY

Methods are disclosed for diagnosing whether toxicity, especially cardiotoxicity, is likely to occur in a patient selected for treatment with a variety of drugs, such as tyrosine kinase inhibitors or erbB inhibitors. Methods are also disclosed for evaluating whether a candidate drug is likely to have a toxic or cardiotoxic affect. In one method lipids, such as triglycerides and cholesterol, can be analyzed to determine whether a fatty acid oxidation disorder is present. In another method enzymes responsible for the observed fatty acid oxidation, such as MCAD, can be determined. With respect to lipid levels it is thought that in normal cells AMP-activated protein kinase activation can lead to a characteristic reduction in the level of lipids and a corresponding increase in glycolytic and shorter carbon chain intermediates, for example of $C_2$ to $C_6$ carbon intermediates. Any statistically significant deviation from the characteristic lipid reduction in normal cells can be considered, for purposes of this disclosure, a fatty acid oxidation disorder. Similarly, with respect to the enzymes involved in these metabolic pathways, any statistically significant change, relative to normal cells, in the amount of activity or levels of these enzymes as measured by Western, Northern, PCR or other techniques, can be considered, for purposes of this disclosure, a fatty acid oxidation disorder. The diagnosis of a fatty acid oxidation disorder can be used to predict an increased risk of toxicity and possibly as a contra-indicator for the use of the drug. Alternatively, in the event a drug is used in a patient having a fatty acid oxidation disorder the methods can be used to indicate the need to closely follow cardiac function in the patient. Alternatively glucose uptake can be measured by known methods, such as by positron emission tomography. In situations where glucose uptake is not diminished or is not diminished to the same extent as in normal noncancerous cells upon administration of a tyrosine kinase inhibitor drug, then the drug treatment is likely to be toxic to the noncancerous cells. Alternatively, if ATP levels decrease more than in normal noncancerous cells upon exposure to a tyrosine kinase inhibitor, then the tyrosine kinase inhibitor is predicted to be toxic.

Another method for predicting whether cardiotoxicity in a patient selected for treatment with a drug, such as tyrosine kinase inhibitor, especially an erbB inhibitor, is to assess the TNFα levels in the patient, either in the tumor or blood or both. The level of TNFα can be used to predict whether a patient is likely to have an adverse event related to cardiotoxicity resulting from drug, particularly HERCEPTIN®, therapy.

Methods are also disclosed for administering drugs that activate AMP activated protein kinase (AMPK), such as certain tyrosine kinase inhibitors, to diminish lipid and fat in patients for cosmetic reasons or weight loss. The method is based on the surprising discovery that activators of AMP activated protein kinase cause a shift in cell metabolism such that lipids are oxidized into smaller carbon intermediates. The metabolic shift results in a surprising reduction in the lipid content of treated cells. Administration of AMP activated protein kinase activators in amounts that are sufficient to activate AMP activated protein kinase can be used to cause cells to loose a portion of their lipid content. Many methods for administering such compounds to cells are known and can be used. Local or systemic administration can be used. Local administration can be by injection, by a skin patch or a salve or lotion.

A method is also disclosed for administering an AMP activated protein kinase activator to a patient, or including it in a medium for incubation with an organ, in an amount that is sufficient to protect organs such as heart muscle and/or brain cells from the acute distress that would normally result from such trauma as ischemia, cytokine release, glucose deprivation and similar events that cause metabolic tension in such cells and organs where such conditions are diagnosed. Dual kinase inhibitors, particularly tyrosine kinase inhibitors that cause an increase in AMP activated protein kinase activity, can also be used. Preferably, such kinase inhibitors will be specific for their targets as described further in the detailed description. Many methods of administration are known and can be used. For example, the drugs can be included in solutions for perfusing organs or can be administered systemically.

A method is also disclosed for preserving an organ for transplant. The method involves preparing a preservation solution comprising an AMPK activator and contacting the organ with the preservation solution. The preservation solution can be any known preservation solution to which an AMPK activator is added in a sufficient amount to provide improved protection for the organ.

Additional features and advantages are described herein, and will be apparent from, the following Detailed Description and the figures.

BRIEF DESCRIPTION OF FIGURES

FIG. 1 is a listing of genes regulated by HERCEPTIN® treatment in Au565 cells.

FIG. 2 are photographs of Au-565 cells treated by NDF or HERCEPTIN® and stained for lipids.

FIG. 3 are photographs of Au-565 cells treated by GW-2974 and stained for lipids.

FIG. 4 are photographs of primary human cardiac myocytes grown under various conditions and stained for lipids.

FIG. 5 is a bar graph illustrating the percentage of human cardiomyocytes testing positive for lipids under various conditions.

FIG. 6 are photographs of MDA-MB-468 cells treated by GW-2974 and intracellular Ca detected by Fluoro-4.

FIG. 7A a photograph of a Western Blot showing the affect of certain tyrosine kinase inhibitors on expression p-eEF2 and p-AMPKα.

FIG. 7B is a photograph of stained cells showing the expression of p-eEF2 in Au565 cells in the presence of various compounds.

FIG. 8 is a photograph of ERRα and MCAD in cardiomyocytes cells with and without treatment by various kinase inhibitors.

DETAILED DESCRIPTION

Figure 9:
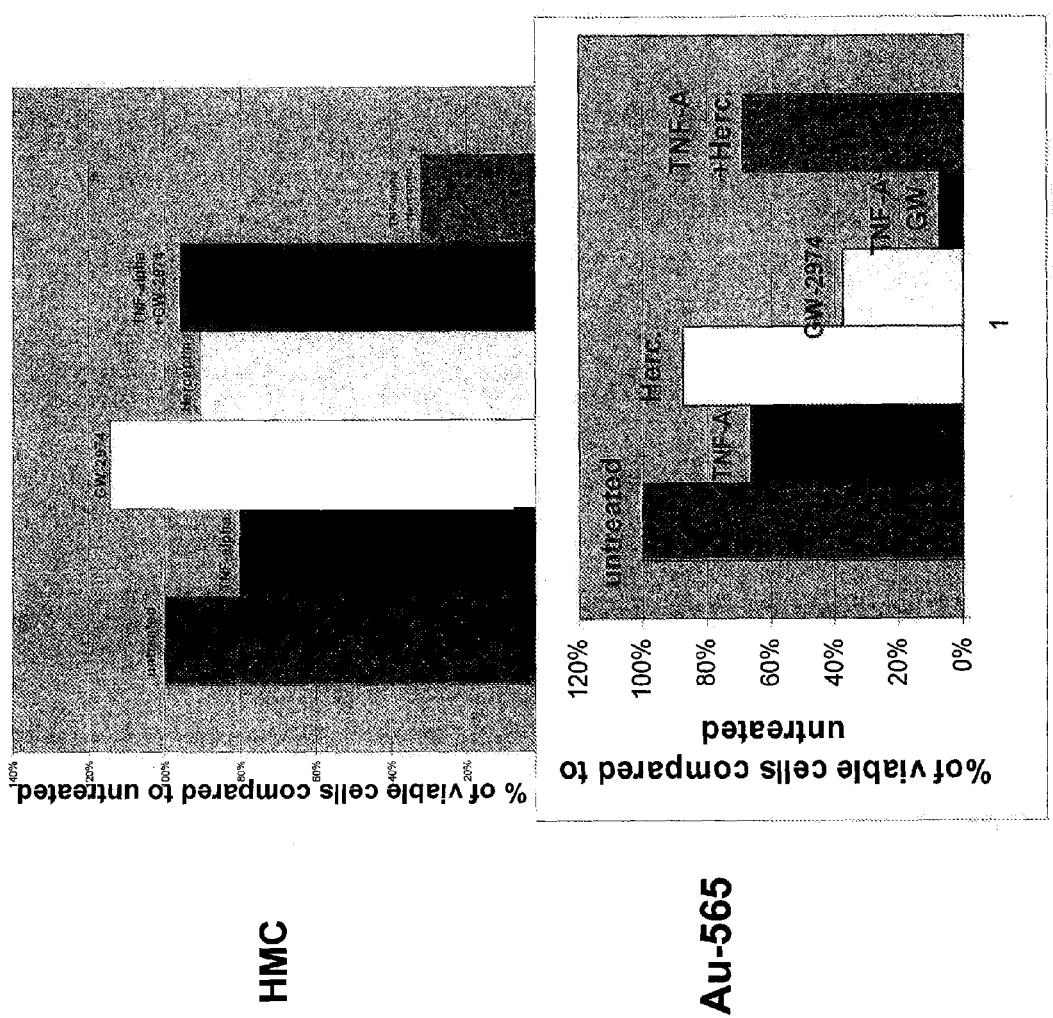
FIG. 9 is a bar graph illustrating the growth inhibition of HMCs treated with combinations of different types of erbB inhibitors and TNFα.
Figure 10:
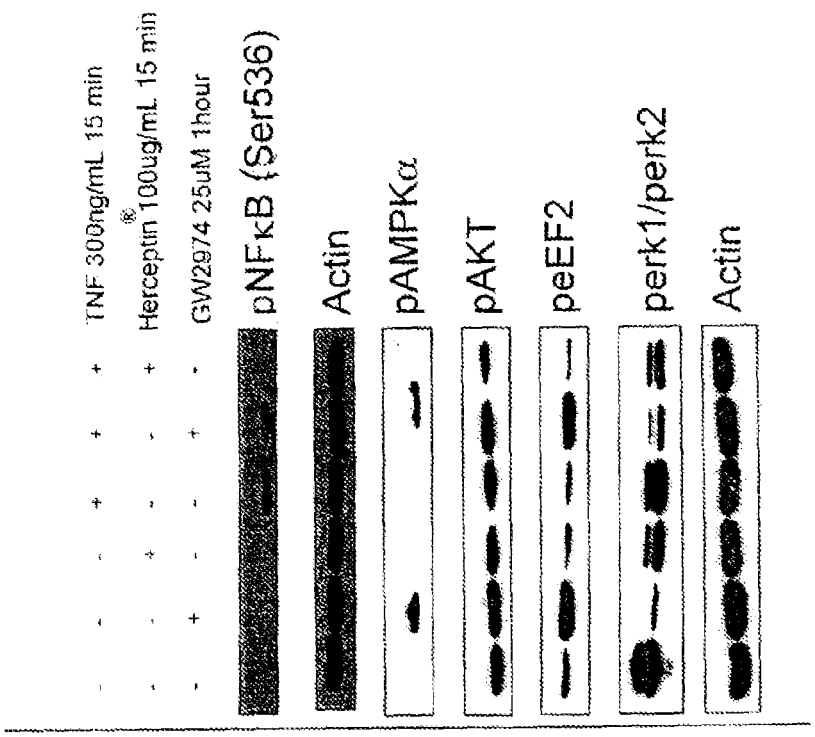
FIG. 10 is a western blot of HMCs probed for NF-κB after treatment with either TNFα; GW2974 or HERCEPTIN® (or combinations).

In one aspect, the present disclosure is based on the discovery that drugs, such as tyrosine kinase inhibitors, like HERCEPTIN® and lapatinib (TYKERB®), affect the expression of genes associated with lipid metabolic pathways and dramatically affect the amount of lipid within the cells. Treatment of otherwise normal cells or cells having normal protein tyrosine kinase regulation with the kinase inhibitors of the invention affects fatty acid metabolism by increasing or decreasing the capacity of such cells to oxidize fatty acids. When normal fat cells grown in culture are exposed to kinase inhibitors such as GW2974, GW572016, the lipid stored within those cells rapidly disappears. This observation has also been made in cardiac cells. Such studies can be conducted using Oil red 0 staining for lipids. Thus, treatment with lapatinib (TYKERB®) and other Her1/Her2 tyrosine kinase inhibitors cause a loss of fat from such cells that is consistent with reduced lipid synthetic rates and/or increased lipid oxidation rates. With other drugs, such as HERCEPTIN®, NDF lipid content appears to increase.

Many kinase inhibitors are also known to be useful as chemotherapeutic agents. In some patients these drugs produce cardiotoxicity. The present disclosure is based on the surprising discovery that cardiotoxicity can be associated with defects in fatty acid metabolism. Thus, patients with certain dysfunctions in fatty acid metabolism or that have high levels of TNFα in blood, and that are undergoing treatment with kinase inhibitors are more likely to suffer from cardiac malfunction such as cardiomyopathy upon treatment with kinase inhibitors such as erbB tyrosine kinase inhibitors. In addition, it has been discovered that patients having high levels of TNFα, or its downstream survival factor NF-κB, in tumor tissue or serum generally have a better response to HERCEPTIN®. This discovery has led to the development of new methods for predicting whether patients will suffer from cardiotoxicity upon treatment with drugs, including kinase inhibitors either alone or in combination with other active agents, that affect phosphorylation states of certain cellular proteins.

A method is disclosed for analyzing a patient's lipids including triglycerides and cholesterol and/or lipid metabolic enzymes such as, MCAD, among others. The results from such analysis can then be used to predict when cardiotoxicity could result from kinase inhibitor treatment and to provide an early indication that cardiac function should be closely monitored in patients undergoing treatment with drugs, such as kinase inhibitors, including HERCEPTIN®, GW572016 or other erbB inhibitors.

The activity of 5-'AMP-activated protein kinase, which has been shown to phosphorylate and inactivate acetyl-CoA carboxylase in other tissues, has been discovered to be significantly increased at the end of ischemia, and remains elevated throughout reperfusion. Accumulation of 5'-AMP during ischemia results in an activation of AMP-activated protein kinase, which phosphorylates and inactivates acetyl-CoA carboxylase during reperfusion. The subsequent decrease in malonyl-CoA levels can result in accelerated fatty acid oxidation rates during reperfusion of ischemic hearts.

With respect to cardiac toxicity, a variety of fatty acid oxidation disorders are known and are listed below in Table I. If such a disorder is detected in a patient it can provide an indication that kinase inhibitors could be toxic to the heart.

TABLE I

Acyl-CoA dehydrogenase deficiencies
Acyl-CoA dehydrogenase, short-chain (SCAD)
Acyl-CoA dehydrogenase, medium-chain (MCAD)
Acyl-CoA dehydrogenase, long-chain (LCAD)
Acyl-CoA dehydrogenase, very long-chain (VLCAD)
2-Enoyl-CoA hydratase deficiency
L-3-Hydroxyacyl-CoA dehydrogenase deficiencies
L-3-Hydroxyacyl-CoA dehydrogenase, short chain (SCHAD)
Trifunctional protein: Long-chain FA (LCHAD)
Alpha subunit (HADHA)
Beta subunit (HADHB)
3-Ketoacyl-CoA thiolase deficiency
3-Ketoacyl-CoA thiolase, Medium chain (MCKAT)
Trifunctional protein
α-Methylacyl-CoA racemase (AMACR) deficiency
Carnitine-acylcarnitine translocase deficiency: 3p21
2,4-Dienoyl-CoA reductase deficiency: 8q21
Electron transfer flavoprotein (ETF) deficiency: 15q23
Ichthyosiform erythroderma (NCIE2): CGI58 gene; 3p21
Trifunctional protein deficiencies: Subunits A & B
Tyrosinemia
1° Disorders of Carnitine metabolism
Fatty acid & Carnitine transport pathways
Fatty acid oxidation pathways
Lipid disorders
Mitochondria: Biochemical abnormalities
Peroxisomal disorders Such disorders can be detected by any suitable method. For example, in certain disorders, fatty acids can be fed to an individual and their metabolism followed. Alternatively, enzyme levels can be determined as in Western blots or mRNA levels for certain gene products can be analyzed, for example. Any detectable decrease provides an indication that a fatty acid oxidation disorder exists and that treatment with a tyrosine kinase inhibitor may be toxic to normal cells and organs.

In a method, patients who are candidates for treatment with kinase inhibitors can be screened for these diseases to determine whether they are likely to suffer myocardiocyte toxicity. For example, the biological macromolecules can be determined in myocardiocytes grown in culture to determine how the levels of these macromolecules are affected by administration of the candidate drug. In a method human myocardiocytes can be grown in culture and the level of phosphorylated AMP-activated protein kinase can be monitored in the presence of the candidate drug. This can be determined by a Western blot that detects the phosphorylated AMP activated kinase.

Without limiting the invention, it is believed that under stress conditions such as hypoxia, ischemia, glucose deprivation, and starvation, an increase in the intracellular AMP:ATP ratio allosterically activates AMP-activated protein kinase (AMPK), a response designed to maintain cellular energy balance. AMP-activated protein kinase was initially discovered to inhibit preparations of acetyl-CoA carboxylase (ACC) and 3-hydroxy-3-methylglutaryl-CoA reductase (HMG-CoA reductase, HMGR). Activation of AMPK is thought to initiate a series of downstream phosphorylation events that switch cells from active ATP consumption (e.g., fatty acid, cholesterol and protein biosynthesis) to ATP production (e.g., fatty acid and glucose oxidation). Stress-induced activation of AMPK is thought to occur following its phosphorylation at threonine 172 on the α subunit by one or more upstream AMPK kinases (AMPKKs), including calmodulin-dependent kinase kinase β (CAMKKβ), a calcium-activated protein kinase, and LKB1, a serine/threonine kinase encoded by the Peutz-Jegher syndrome tumor suppressor gene. Activation of AMPK in skeletal muscle and heart is believed to lead to the phosphorylation and inhibition of acetyl-CoA carboxylase (ACC), which in turn is thought to reduce the level of malonyl-CoA, itself an inhibitor of carnitine palmitoyltransferase 1 (CPT 1). De-repression of CPT 1 is thought to cause the concomitant increase in β-oxidation of fatty acid, which is thought to lead to increased mitochondrial production of ATP. Stress-induced activation of AMPK is also thought to inhibit protein synthesis by inhibiting mTOR and directly modulating eEF2, a translation elongation factor known to be associated with cardiac protection. Importantly, alteration in mitochondrial function is thought to lead to cardiomyocyte death by imatinib. Moreover, inhibition of cap-dependent translation via AMPK-mediated TSC2 phosphorylation is thought to be extremely important for cell survival in response to ATP depletion. Increased biosynthesis of, rather than consumption of ATP following AMPK activation may also protect cardiomyocytes against ischemic injury.

It has been discovered that molecules such as GW2974, a potent small molecule HER2/EGFR tyrosine kinase inhibitor with a similar activity profile to lapatinib, that can activate AMPK and its downstream substrates stimulate fatty acid oxidation, which in turn increases ATP production in HER2-expressing human cardiomyocytes, protecting against apoptosis induced by TNFα, a known cytokine detected in cardiac failure. Conversely, molecules such as trastuzumab that do not activate AMPK result in enhanced cardiomyocyte cell death in response to TNFα. The effects of specific HER2-targeted therapies on AMPK and consequently energy production may predict for the risk associated cardiomyopathy and provide a novel HER2-directed therapeutic strategy to protect myocardium from the killing effects of TNFα or other pro-apoptotic stimuli, following acute ischemic injury.

In addition, tyrosine kinase inhibitors can be used to reduce fat in cells, particularly cells that are otherwise normal or that lack protein tyrosine kinase activity mediated disease. To this end at least a portion of a mammal or tissue can be treated with a kinase inhibitor such that the amount of lipid in the cells is reduced. Any suitable kinase inhibitor can be used. Methods for determining suitable inhibitors are well known. For example, samples of adipocytes can be grown in the presence and absence of a kinase inhibitor and stained with Oil red 0 by known methods to determine whether the kinase inhibitor causes a reduction in stored fat. Those kinase inhibitors that cause an observable reduction in fat storage are suitable for the present invention. Exemplary kinase inhibitors that are suitable for the invention include erbB inhibitors, especially including GW2974, GW572016, and the like. Table II below shows the reduction in lipid content obtained by treatment with GW2974. Au565 cells were grown under normal conditions known in the art and treated for 2 days with GW2974 (25 μM). The cells were collected, washed and sonicated in water (2,000,000 cells in 200 μL of water). The cells were spun down and were tested for acylcarnitines (byproducts of mitochondrial fatty acid oxidation) by MS/MS for intraceullar metabolites.

TABLE II

| | Acylcarnitines (pmoles of protein) | | |
|---|---|---|---|
| | C18:1 | C16 | C2 |
| Control (Cell pellet) | 8.56 | 4.09 | 148.54 |
| GW2974 (Cell pellet) | 4.1 | 0.83 | 258.88 |

In a method cells can be treated with suitable kinase inhibitors to reduce lipid storage. The method can include the steps of contacting the cells with a sufficient amount of a suitable tyrosine kinase inhibitor to cause the cell to rid itself of an amount and preferably most or, more preferably, virtually all of its surplus of stored lipids. The cells can be in an in vitro cell culture or can be located in an individual. The method is particularly effective when used on cells that are disease free or free from protein tyrosine kinase activity related diseases.

Methods are also disclosed for administering a kinase inhibitor, such as a tyrosine kinase inhibitor or dual tyrosine kinase inhibitor, to a patient, such as during heart reperfusion or during a heart attack, in order to counteract the fatty acid oxidation effect and protect the heart muscle and/or brain cells. Such treatments can be used to protect heart cells, brain cells and cells from other tissues and organs from acute distress caused by ischemia, cytokine release, glucose deprivation or other maladies that metabolically stress such cells.

Preferably the kinase inhibitors are specific in that they cause a shift in metabolic activity and do not affect unrelated targets. The specificity of various kinase inhibitors can be determined by methods described in Fabian et al., *A small molecule-kinase interaction map for clinical kinase inhibitors*, Nature Biotechnology 23, p. 329 which is incorporated by reference. It is believed that the shift in metabolic activity is brought about through an increase in AMP activated protein kinase activity.

The active agent can be administered to an individual orally, locally by injection or through a skin patch, a salve or a lotion or can be administered parenterally so long as it reaches the intended target cells in a sufficient amount to exert its lipid reducing effect. For example, it is preferred to administer the AMP activated protein kinase activator locally in a tissue such as adipose tissue that stores lipid to cause a reduction in lipid content. It may be administered systemically to patients in need of treatment for metabolic stress, heart attack, ischemia and the like.

The AMP activated protein kinase activators can be administered as salts or solvates or as free chemicals, however, it is preferred to administer the inhibitors in the form of a pharmaceutical formulation. The formulation can contain, in addition to the active agent, one or more pharmaceutically acceptable carriers, diluents or excipients.

The pharmaceutical formulations can be presented in unit dose forms containing a predetermined amount of active ingredient per unit dose. Such a unit can contain for example 0.5 mg to 1 g, preferably 70 mg to 700 mg, more preferably 5 mg to 100 mg of active agent depending on the route of administration and the age, weight and condition of the patient. For example, in mice, 100 mg/kg of GW2974 can be administered to preserve the heart during a period of starvation.

Pharmaceutical formulations can be adapted for administration by any appropriate route, for example by the oral (including buccal or sublingual), rectal, nasal, topical (including buccal, sublingual or transdermal), vaginal or parenteral (including subcutaneous, intramuscular, intravenous or intradermal) route. Such formulations can be prepared by any method known in the art of pharmacy, for example by bringing into association the active ingredient with the carrier(s) or excipient(s).

Pharmaceutical formulations adapted for oral administration can be in the form of capsules or tablets; powders or granules; solutions or suspensions in aqueous or non-aqueous liquids; edible foams or whips; or oil-in-water liquid emulsions or water-in-oil liquid emulsions and in liposomes.

Pharmaceutical formulations for transdermal administration can be presented as discrete patches intended to remain in intimate contact with the skin of the recipient for a prolonged period of time. The active ingredient can be delivered from the patch by iontophoresis by known methods.

Pharmaceutical formulations for topical administration can be formulated as ointments, creams, suspensions, lotions, powders, solutions, pastes, gels, sprays, aerosols or oils.

For treatments of the external tissues the formulations can be applied as a topical ointments or creams. When formulated in an ointment, the active agent can be employed with either a paraffinic or a water-miscible ointment base. Alternatively, the active agent can also be formulated in a cream with an oil-in-water cream base or a water-in-oil base. Preferably, such ointments will allow the active agent to penetrate the skin and contact target cells and tissues, particularly for the amelioration of fat in fat laden tissue and organs.

Pharmaceutical formulations adapted for topical administration in the mouth include lozenges, pastilles and mouth washes.

Pharmaceutical formulations for administration by inhalation include fine particle dusts or mists which can be generated by means of various types of metered dose pressurised aerosols, nebulizers or insufflators.

Pharmaceutical formulations for vaginal administration can be presented as pessaries, tampons, creams, gels, pastes, foams or spray formulations.

Pharmaceutical formulations for parenteral administration can include aqueous and non-aqueous sterile injection solutions which can further include anti-oxidants such as tocopherol, buffers, bacteriostats and solutes to make the formulation isotonic with the blood of the intended recipient; and aqueous and non-aqueous sterile suspensions which can include suspending agents and thickening agents.

Formulations can be presented in unit-dose or multi-dose containers, for example sealed ampoules and vials, and can be stored in a freeze-dried (lyophilized) condition requiring only the addition of the sterile liquid carrier, for example water for injections, immediately prior to use. Extemporaneous injection solutions and suspensions can be prepared from sterile powders, granules and tablets.

Preferred unit dosage formulations are those containing a daily dose or sub-dose, or an appropriate fraction of an active ingredient.

It should be understood that in addition to the ingredients particularly mentioned above, the formulations can include other agents conventional in the art having regard to the type of formulation in question, for example those suitable for oral administration can include flavoring agents.

The animal requiring treatment with a compound, salt or solvate of the present invention is usually a mammal, such as a human being.

Therapeutically effective amounts of the active agent, salt or solvate of the present invention will depend upon a number of factors including, for example, the age and weight of the animal, the severity of the condition requiring treatment, the nature of the formulation, and the route of administration, and will ultimately be at the discretion of the attendant physician or veterinarian. However, an effective amount of a compound of the present invention for the treatment of toxicity, will generally be in the range of 0.1 to 500 mg/kg body weight of recipient (mammal) per day and more usually in the range of 1 to 200 mg/kg body weight per day. Thus, for a 70 kg adult mammal, the actual amount per day would usually be from 70 to 700 mg and this amount can be given in a single dose per day or any number of sub-doses per day such that the total daily dose is the same. An effective amount of a salt or solvate of the present invention can be determined as a proportion of the effective amount of the compound per se.

The compounds of the present invention and their salts and solvates can be employed alone or in combination with other therapeutic agents. Combination therapies according to the present invention thus comprise the administration of at least one AMP activated protein kinase activator of the invention or a pharmaceutically acceptable salt or solvate thereof and at least one other pharmaceutically active agent, such as a cancer therapeutic. Combination actives can be administered together or separately and, when administered separately can be administered simultaneously or sequentially in any order. The amounts of the kinase inhibitor of the invention and the other pharmaceutically active agent(s) and the relative timings of administration will be selected in order to achieve the desired combined therapeutic effect.

EXAMPLE 1

The following example demonstrates the identification of genes that are affected by treatment of HERCEPTIN® in an in vitro cell culture of Au565 cells. Au565 cells were grown under normal conditions and treated with HERCEPTIN® or left untreated. Cells were pelleted, snap frozen in liquid nitrogen and analyzed in a microarray using standard conditions. Cy3 and Cy5 labeled cDNA was prepared from RNA isolated from the cell pellets. Genes involved in lipid metabolism are shown in Table III. Genes involved in other pathways that were either upregulated or downregulated are also shown in FIG. 1.

TABLE III

Changes in Metabolic Genes by Microarray Analysis of Au565 Cells That Were Untreated or Treated with HERCEPTIN ®

| Gene | Description | Relative change in HERCEPTIN ® treated cells compared with untreated cells |
|---|---|---|
| NKX2-5 | Cardiac specific homeobox, a transcription factor involved in heart development and possibly in apoptosis; mutations in the corresponding gene are associated with congenital heart disease, septal and conduction defects, and tetralogy of Fallot | 4.71x |
| ESRR6 | Estrogen-related receptor gamma, binds to estrogen response elements and activates transcription in a ligand-independent manner, can have roles in tissue differentiation and maintenance | 4.18x |
| FABP1 | Fatty acid binding protein 1 liver, positive regulator of peroxisome proliferators activated receptor alpha (PPARA), plays a role in fatty acid transport, cell proliferation, and apoptosis, increased expression is associated with prostate cancer | −6.29x |
| NRG1 | Neuregulin 1, a secreted protein, activates ERBB2 and other members of the EGF receptor family of tyrosine kinase receptors, induces cell migration, cell proliferation and neurogenesis; gene amplification is associated with some breast tumors | −5.07x |
| PERC | PGC-1 related estrogen receptor alpha coactivator (PPAR gamma coactivator 1 beta), a transcriptional coactivator that binds and activates nuclear hormone receptors, can play a role in gluconeogenesis or fatty acid oxidation | −5.20x |
| ERBB4 | Avian erythroblastosis oncogene B4, a receptor tyrosine kinase of the EGF receptor family, activated by neuregulin ligands, plays a role in cell migration, proliferation, and differentiation, involved in the pathogenesis of multiple malignant neoplasias | 4.48x |
| | | Log Ratio |
| BBOX1 | Butyrobetaine (gamma) 2-oxoglutarate dioxygenase (gamma-butyrobetaine hydroxylase) 1, catalyzes the conversion of gamma butyrobetaine to L-carnitine in carnitine biosynthesis | 5.13E−01 |
| GLS | Kidney-type glutaminase, catalyzes the hydrolysis of glutamine to glutamate and ammonia, provides TCA cycle intermediates, helps maintain acid-base balance, produces neurotransmitters, and initiates glutamine catabolism | 5.12E−01 |
| IQGAP2 | IQ motif containing GTPase activating protein 2, inhibits GTPase activity of CDC42 and RAC1, can bind actin and play a role in Rho-family GTPase regulation of cell shape | 4.85E−01 |
| TRPM4 | Transient receptor potential cation channel subfamily M member 4, a Ca2+-activated channel permeable to monovalent cations, responsive to G protein-coupled receptor-mediated Ca2+ elevation, inhibits Ca2+ influx through membrane potential depolarization | 4.43E−01 |
| SAT | Spermidine/spermine N1-acetyltransferase, catalyzes the rate limiting step of polyamine catabolism, promotes polyamine homeostasis, involved in oxidative stress and heat shock responses, modulates tumorigenicity and sensitivity to some anticancer drugs | 4.04E−01 |
| I_1152020 | Protein containing three collagen triple helix repeats, which are found in some extracellular proteins, and a C-terminal C1q domain, has moderate similarity to mouse Acrp30, which controls energy balance, insulin sensitivity, and adipocyte | 4.00E−01 |
| CLSP | Calmodulin-like skin protein, a member of the calmodulin family of calcium-binding proteins, can play a role in keratinocyte differentiation, shows altered expression in sun-damaged skin | −4.03E−01 |
| ME1 | Malic enzyme 1, catalyzes the oxidative decarboxylation of malate to form pyruvate and can play a role lipogenesis; variant can be associated with breast cancer | −4.04E−01 |
| ACAT2 | Homo sapiens acetyl-Coenzyme A acetyltransferase 2 (acetoacetyl Coenzyme A thiolase) (ACAT2), mRNA | −4.33E−01 |

TABLE III-continued

Changes in Metabolic Genes by Microarray Analysis of Au565 Cells
That Were Untreated or Treated with HERCEPTIN ®

| Gene | Description | |
|---|---|---|
| ACAT2 | Acetyl-Coenzyme A acetyltransferase 2 (cytosolic acetoacetyl Coenzyme A thiolase), a liver enzyme that functions in acyl-CoA metabolism | −5.30E−01 |
| ACAT2 | Homo sapiens acetyl-Coenzyme A acetyltransferase 2 (acetoacetyl Coenzyme A thiolase) (ACAT2), mRNA | −4.33E−01 |
| ACAT2 | Acetyl-Coenzyme A acetyltransferase 2 (cytosolic acetoacetyl Coenzyme A thiolase), a liver enzyme that functions in acyl-CoA metabolism | −5.30E−01 |
| ALDOA | Aldolase A (fructose-bisphosphate aldolase), catalyzes cleavage or condensation of fructose-1,6-bisphosphate into dihydroxyacetonephosphate and glyceraldehyde-3-phosphate in glycolysis, deficiency manifests as hemolytic anemia and metabolic myopathy | −4.54E−01 |
| NFκBIL2 | NF-kappaB inhibitor-like 2, member of IkappaB family, inhibits DNA binding of NFKB1-RELA NF-kappaB heterodimers and NFKB1 homodimers, NF-kappaB-mediated transcription from Igkappa enhancer, and can regulate NF-kappaB function in epithelial cells | −4.90E−01 |
| ENO1 | Enolase 1 (alpha enolase), converts 2-phospho-D-glycerate to phosphoenolpyruvate in glycolysis, an autoantigen in multiple autoimmune diseases, shorter alternative form c-myc promoter binding protein (MPB1) is a transcriptional repressor | −5.01E−01 |
| GSTT2 | Glutathione S-transferase theta 2, theta class glutathione transferase and peroxidase, involved in xenobiotic metabolism, can be involved in detoxification of fatty acid hydroperoxides and play a role in cancer prevention by inactivating carcinogens | −5.33E−01 |
| APOL1 | Apolipoprotein L, a component of large, apoA-I(APOA1)-containing, high density lipoproteins, can be involved in lipid transport and metabolism; elevated expression in prefrontal cortex is associated with schizophrenia | −6.43E−01 |
| AKR1C2 | Aldo keto reductase family 1 member C2 (dihydrodiol dehydrogenase), functions in bile transport, steroid metabolism, and xenobiotic metabolism, can play a role in behavior modification mediated by selective serotonin reuptake inhibitors | −7.44E−01 |
| AKR1C2 | Aldo keto reductase family 1 member C2 (dihydrodiol dehydrogenase), functions in bile transport, steroid metabolism, and xenobiotic metabolism, can play a role in behavior modification mediated by selective serotonin reuptake inhibitors | −8.23E−01 |
| CAMK4 | Calcium/calmodulin-dependent protein kinase IV, a protein kinase involved in Ca(2+)-regulated gene expression, including CREBBP-dependent gene expression | 4.46E−01 |
| FKSG14 | Protein with high similarity to SoxLZ-Sox6 leucine zipper binding protein in testis (mouse Solt), which binds SoxLZ/Sox6 and enhances SoxLZ/Sox6-mediated transcription activation along with calcium/calmodulin-dependent protein kinase IV (mouse Camk4) | −4.57E−01 |
| SOAT1 | Acyl-Coenzyme A:cholesterol acyltransferase, synthesizes cholesterol esters from cholesterol and long-chain fatty acyl-coenzyme A, acts in lipoprotein metabolism, cholesterol homeostasis, and monocyte differentiation; associated with atherosclerosis | −4.05E−01 |
| I_962304.FL1 | Potassium voltage-gated channel (Shal-related subfamily, member 1), predicted to generate A-type transient outward K+ currents that are important for the control of excitability of neurons and cardiac cells [647-aa form] | −4.16E−01 |
| SCN2A2 | Sodium channel voltage gated type II alpha 2, displays voltage-dependent and sodium-selective current, can play a role in the rising phase of action potential in excitable cells, sensitive to tetrodotoxin | 4.54E−01 |
| SCN1A | Sodium channel voltage-gated type I (alpha subunit), a voltage-sensitive sodium channel; mutations are associated with severe myoclonic epilepsy of infancy and generalized epilepsy with febrile seizures plus | 4.14E−01 |
| SCN11A | Sodium channel voltage-gated type XI alpha polypeptide, a putative voltage-sensitive sodium channel that can produce tetrodotoxin-resistant sodium | 4.02E−01 |

TABLE III-continued

Changes in Metabolic Genes by Microarray Analysis of Au565 Cells That Were Untreated or Treated with HERCEPTIN ®

| Gene | Description | |
|---|---|---|
| | currents in peripheral sensory neurons, can play a role in pain transmission and neuropathic pain in . . . | |
| FASN | Fatty acid synthase, multifunctional enzyme that synthesizes fatty acids from dietary proteins and carbohydrates, increased expression is associated with various cancers and inhibition can be therapeutic for breast and prostate cancer | −4.29E−01 |
| ELOVL2 | Homo sapiens elongation of very long chain fatty acids (FEN1/Elo2, SUR4/Elo3, yeast)-like 2 (ELOVL2), mRNA | −4.36E−01 |
| HPCAL1 | Hippocalcin-like 1, a putative calcium-sensing protein, member of the neural visinin-like (NVP) family of calcium-binding proteins, localized to axons and dendrites, can play a role in neuronal signaling in the central nervous system | −4.53E−01 |
| KCNG2 | Potassium voltage channel subfamily gamma 2, a member of the Kv6 family of ion channels, functions as a votage-gated potassium channel upon interaction with Kv2.1 alpha subunit, can contribute to cardiac action potentiation repolarization | −5.53E−01 |
| CCL14 | Small inducible cytokine subfamily A member 14, a chemoattractant that enhances proliferation of mycloid progenitor cells and can affect replication of the HIV 1 virus, can play a role in AIDS pathogenesis and chemokine receptor CCR1 associated diseases | −4.49E−01 |
| CLCA1 | Calcium-activated chloride channel 1, a chloride channel which plays a role in mucous production in mucoepidermal cells and can function as a tumor suppressor; dysregulation can contribute to asthma and the progression of colorectal cancer | −6.70E−01 |
| FABP1 | Fatty acid binding protein 1 liver, positive regulator of peroxisome proliferator activated receptor alpha (PPARA), plays a role in fatty acid transport, cell proliferation, and apoptosis, increased expression is associated with prostate cancer | −7.22E−01 |
| BBOX1 | Butyrobetaine (gamma) 2-oxoglutarate dioxygenase (gamma-butyrobetaine hydroxylase) 1, catalyzes the conversion of gamma butyrobetaine to L-carnitine in carnitine biosynthesis | 5.13E−01 |
| GLS | Kidney-type glutaminase, catalyzes the hydrolysis of glutamine to glutamate and ammonia, provides TCA cycle intermediates, helps maintain acid-base balance, produces neurotransmitters, and initiates glutamine catabolism | 5.12E−01 |
| IQGAP2 | IQ motif containing GTPase activating protein 2, inhibits GTPase activity of CDC42 and RAC1, can bind actin and play a role in Rho-family GTPase regulation of cell shape | 4.85E−01 |
| TRPM4 | Transient receptor potential cation channel subfamily M member 4, a Ca2+-activated channel permeable to monovalent cations, responsive to G protein-coupled receptor-mediated Ca2+ elevation, inhibits Ca2+ influx through membrane potential depolarization | 4.43E−01 |
| SAT | Spermidine/spermine N1-acetyltransferase, catalyzes the rate limiting step of polyamine catabolism, promotes polyamine homeostasis, involved in oxidative stress and heat shock responses, modulates tumorigenicity and sensitivity to some anticancer drugs | 4.04E−01 |
| I_1152020 | Protein containing three collagen triple helix repeats, which are found in some extracellular proteins, and a C-terminal C1q domain, has moderate similarity to mouse Acrp30, which controls energy balance, insulin sensitivity, and adipocyte | 4.00E−01 |

EXAMPLE 2

This example demonstrates that adipocytes lose lipid when treated with a small molecule tyrosine kinase inhibitor, GW2974. FIG. 2 shows that Au565 cells treated with either an ErbB stimulatory ligand, NDF, or the monoclonal antibody HERCEPTIN®, both result in the production of lipids. This is shown by the staining of lipids with oil red (lipids are represented by red dots) against the background counterstaining of the cells (hematoxylin). FIG. 3 shows that lipids are present in untreated Au565 cells but are reduced in cells treated with the dual EGFR and ErbB2 inhibitor, GW2974. FIG. 4 shows cardiomyocyte cells treated with either GW2974, Herceptin or NDF. Lipids increase in cells treated with Herceptin and NDF (compared with untreated cells) but not decrease in cells treated with GW2974. FIG. 5 shows a quantitative measure of lipids in control, HERCEPTIN® and GW2974 treated cells.

Treatment of cells with GW2974 causes a redistribution of intracellular calcium (FIG. 6). This can be seen in MDA-MB-468 breast cancer cells where calcium is detected by fluorescently by Fluoro-4. This redistribution of calcium results in the activation and phosphorylation of AMPK. Activated AMPK represses translation by phosphorylation of the translation factor eEF-2 (FIG. 7), which inactivates eEF-2 and represses protein synthesis, a known effect of TKIs. FIG. 7A shows a western blot of Au565 cells treated with either a stimulatory ligand (EGF) or GW2974 and probed for p-eEF-2. p-eEF-2 is dramatically increased after GW2974 treatment. FIG. 7B shows expression of p-eEF-2 by IHC. C225 and HERCEPTIN® do not increase p-eEF-2, however TKIs like Iressa, GW2974 and rapamycin do.

ERRα plays a role in lipid metabolism in cardiac cells, and MCAD is an enzyme that breaks down lipids and fatty acids. Mutations in MCAD is a common genetic disorder, especially in those of northern European descent. FIG. 8 shows that in HERCEPTIN® treated cells, the level of ERRα diminished slightly. MCAD is expressed in HERCEPTIN® treated cells but is completely absent from GW2974 treated cells.

EXAMPLE 3

The following example demonstrates the change in mRNA expression profile of cells treated with GW2974.

Au565 cells were grown under normal conditions and were untreated or treated with GW2974 (25 μM). Cells were pelleted, snap frozen in liquid nitrogen and subjected to microarray analysis. RNA was isolated using the Agilent Total RNA Isolation Kit. Cy3 and Cy5 labeled cRNA was prepared using the Agilent Low RNA Input Fluorescent Linear Amplification Kit. Labeled cRNAs were hybridized to a G4110A Human 1A(V2) microarray consisting of 60-mer oligonucleotides representing over 18K well-characterized, full length, human genes. Table IV provides the results in Table form.

TABLE IV

| Gene Name | Description | GW2974 change compared to control |
|---|---|---|
| | TABLE IV A - Ion Channel | |
| FLJ12476 | Protein containing an IQ calmodulin-binding domain | 5.0x |
| CAMK4 | Calcium/calmodulin-dependent protein kinase IV, a protein kinase involved in Ca(2+)-regulated gene expression, including CREBBP-dependent gene expression | 4.5x |
| AVIL | Protein with high similarity to villin 1 (human VIL1), which is a calcium-regulated actin-binding protein that caps, severs, and bundles actin filaments, member of the gelsolin family and contains a villin headpiece domain | 4.2x |
| SCN1A | Sodium channel voltage-gated type I (alpha subunit), a voltage-sensitive sodium channel; mutations are associated with severe myoclonic epilepsy of infancy and generalized epilepsy with febrile seizures plus | 4.1x |
| CLSP | Calmodulin-like skin protein, a member of the calmodulin family of calcium-binding proteins, may play a role in keratinocyte differentiation, shows altered expression in sun-damaged skin | −4.0x |
| GNB5 | Guanine nucleotide binding protein (G protein) beta 5, a component of heterotrimeric G protein complexes that transduce signals from G protein-coupled receptors to downstream effector proteins, may regulate calcium channel activity | −4.1x |
| KCNK6 | Potassium channel subfamily K member 6 (TWIK-2), a pH-sensitive outward and mild inward rectifying member of the tandem pore domain K+ channel family, may play a role in setting the cellular resting membrane potential and in cardiac cell excitability | −4.1x |
| CASK | Calcium/calmodulin-dependent serine protein kinase, member of the MAGUK family, involved in recruiting multiprotein complexes at the plasma membrane, may link the extracellular matrix to the actin cytoskeleton, may regulate synaptic vesicle exocytosis | −4.2x |
| I_962304.FL1 | Potassium voltage-gated channel (Shal-related subfamily, member 1), predicted to generate A-type transient outward K+ currents that are important for the control of excitability of neurons and cardiac cells [647-aa form] | −4.2x |
| CD38 | CD38 antigen, has both cyclic ADP-ribose-forming and -hydrolyzing activities, regulates intracellular calcium mobilization, may play a role in superantigen-induced T cell proliferation, autoantibodies may contribute to noninsulin dependent diabetes | −4.4x |
| HPCAL1 | Hippocalcin-like 1, a putative calcium-sensing protein, member of the neural visinin-like (NVP) family of calcium-binding proteins, localized to axons and dendrites, may play a role in neuronal signaling in the central nervous system | −4.5x |

TABLE IV-continued

| Gene Name | Description | GW2974 change compared to control |
|---|---|---|
| FKSG14 | Protein with high similarity to SoxLZ-Sox6 leucine zipper binding protein in testis (mouse Solt), which binds SoxLZ/Sox6 and enhances SoxLZ/Sox6-mediated transcription activation along with calcium/calmodulin-dependent protein kinase IV (mouse Camk4) | −4.6x |
| CCR2 | CC chemokine receptor 2, a G protein-coupled receptor that binds CC subfamily chemokines and mediates chemotaxis and intracellular calcium flux; variants of CCR2 may confer increased survival after human immunodeficiency virus infection | −5.0x |
| FREQ | Frequenin homolog (*Drosophila*), a calcium-binding protein and putative kinase inhibitor, binds and modulates the activity of KV4 K+ channels in a Ca2+-dependent manner, may have a regulatory role in secretion | −5.3x |
| STK33 | Serine-threonine protein kinase 33, a putative serine-threonine kinase that may be a member of the calcium/calmodulin-dependent protein kinase family | −5.3x |
| S100A9 | S100 calcium-binding protein A9 (calgranulin B), part of a complex (27e10 antigen) with S100A8 that activates beta2 integrin (ITGB2) ligand binding, thereby mediating neutrophil adhesion during inflammation, binds and transports fatty acids | −5.5x |
| KCNG2 | Potassium voltage channel subfamily gamma 2, a member of the Kv6 family of ion channels, functions as a votage-gated potassium channel upon interaction with Kv2.1 alpha subunit, may contribute to cardiac action potentiation repolarization | −5.5x |
| CLCA1 | Calcium-activated chloride channel 1, a chloride channel which plays a role in mucous production in mucoepidermal cells and may function as a tumor suppressor; dysregulation may contribute to asthma and the progression of colorectal cancer | −6.7x |
| AKAP5 | A kinase anchor protein 5, anchors cAMP-dependent protein kinase to postsynaptic densities by binding the type 2 regulatory subunits, PRKAR2A and PRKAR2B, and by this may regulate postsynaptic events; also binds calmodulin and protein kinase C | −7.3x |

Table IV B - Cardiac regulation

| Gene Name | Description | GW2974 change compared to control |
|---|---|---|
| PRKG1 | cGMP-dependent protein kinase type 1, relaxes vascular smooth muscle and inhibits platelet aggregation, may be involved cardiac contractility, may be associated with hypertension and atherosclerosis; mouse Prkg1 is associated with erectile dysfunction | 6.51x |
| TGFβ1 | Transforming growth factor beta induced 68 kDa (kerato-epithelin), extracellular adhesion protein induced by transforming growth factor beta (TGFB1), may play roles in osteogenesis and lung structure/function; gene alteration causes corneal dystrophies | 5.31x |
| NRXN3 | Neurexin 3, member of the neurexin family of synaptic cell surface proteins and a putative integral membrane protein which may have a role in axon guidance, cardiac isoform may form a complex with dystroglycan and mediate intercellular connections | 4.58x |
| KCNK6 | Potassium channel subfamily K member 6 (TWIK-2), a pH-sensitive outward and mild inward rectifying member of the tandem pore domain K+ channel family, may play a role in setting the cellular resting membrane potential and in cardiac cell excitability | −4.08x |
| I_962304.FL1 | Potassium voltage-gated channel (Shal-related subfamily, member 1), predicted to generate A-type transient outward K+ currents that are important for the control of excitability of neurons and cardiac cells [647-aa form] | −4.16x |
| KCNG2 | Potassium voltage channel subfamily gamma 2, a member of the Kv6 family of ion channels, functions as a votage-gated potassium channel upon interaction with Kv2.1 alpha subunit, may contribute to cardiac action potentiation repolarization | −5.53x |

TABLE IV-continued

| Gene Name | Description | GW2974 change compared to control |
|---|---|---|
| | Table IV C - Fatty acid and amino acid metabolism | |
| PRKG1 | cGMP-dependent protein kinase type 1, relaxes vascular smooth muscle and inhibits platelet aggregation, may be involved cardiac contractility, may be associated with hypertension and atherosclerosis; mouse Prkg1 is associated with erectile dysfunction | 6.5x |
| BBOX1 | Butyrobetaine (gamma) 2-oxoglutarate dioxygenase (gamma-butyrobetaine hydroxylase) 1, catalyzes the conversion of gamma butyrobetaine to L-carnitine in carnitine biosynthesis | 5.1 |
| GLS | Kidney-type glutaminase, catalyzes the hydrolysis of glutamine to glutamate and ammonia, provides TCA cycle intermediates, helps maintain acid-base balance, produces neurotransmitters, and initiates glutamine catabolism | 5.1 |
| NRXN3 | Neurexin 3, member of the neurexin family of synaptic cell surface proteins and a putative integral membrane protein which may have a role in axon guidance, cardiac isoform may form a complex with dystroglycan and mediate intercellular connections | 4.6x |
| CYP2C8 | Cytochrome P450 subfamily IIC (mephenytoin 4-hydroxylase) polypeptide 8, a member of heme-binding monooxygenase superfamily that metabolizes steroids, fatty acids, and xenobiotics; hepatic expression is upregulated by rifampin treatment | 4.5x |
| SAT | Spermidine/spermine N1-acetyltransferase, catalyzes the rate limiting step of polyamine catabolism, promotes polyamine homeostasis, involved in oxidative stress and heat shock responses, modulates tumorigenicity and sensitivity to some anticancer drugs | 4.4 |
| SOAT1 | Acyl-Coenzyme A: cholesterol acyltransferase, synthesizes cholesterol esters from cholesterol and long-chain fatty acyl-coenzyme A, acts in lipoprotein metabolism, cholesterol homeostasis, and monocyte differentiation; associated with atherosclerosis | −4.0x |
| KCNK6 | Potassium channel subfamily K member 6 (TWIK-2), a pH-sensitive outward and mild inward rectifying member of the tandem pore domain K+ channel family, may play a role in setting the cellular resting membrane potential and in cardiac cell excitability | −4.1x |
| I_962304.FL1 | Potassium voltage-gated channel (Shal-related subfamily, member 1), predicted to generate A-type transient outward K+ currents that are important for the control of excitability of neurons and cardiac cells [647-aa form] | −4.2x |
| HSPA8 | Heat shock 70 kD protein 8, a constitutively expressed member of the heat shock HSP70 family of molecular chaperones; expression is elevated in the hearts of patients with hypertrophic cardiomyopathy | −4.2x |
| FASN | Fatty acid synthase, multifunctional enzyme that synthesizes fatty acids from dietary proteins and carbohydrates, increased expression is associated with various cancers and inhibition may be therapeutic for breast and prostate cancer | −4.3x |
| ELOVL2 | Homo sapiens elongation of very long chain fatty acids (FEN1/Elo2, SUR4/Elo3, yeast)-like 2 (ELOVL2), mRNA | −4.4x |
| PFKL | Liver phosphofructokinase, catalyses the phosphorylation of fructose-6-phosphate to fructose-1,6-bisphosphate in blycolysis, deficiency is linked to glycogenosis type VII while overexpression may lead to the cognitive diabilities of Downs syndrome | −4.7 |
| LDLR | Low density lipoprotein receptor, mediates uptake of low density lipoproteins, involved in lipid metabolism; gene variations are associated with familial hypercholesterolemia, hypertension, atherosclerosis, and coronary artery disease | −5.2x |
| GSTT2 | Glutathione S-transferase theta 2, theta class glutathione transferase and peroxidase, involved in xenobiotic metabolism, may be involved in detoxification of fatty acid hydroperoxides and play a role in cancer prevention by inactivating carcinogens | −5.3 |

TABLE IV-continued

| Gene Name | Description | GW2974 change compared to control |
|---|---|---|
| ACAT2 | Acetyl-Coenzyme A acetyltransferase 2 (cytosolic acetoacetyl Coenzyme A thiolase), a liver enzyme that functions in acyl-CoA metabolism | −5.3 |
| S100A9 | S100 calcium-binding protein A9 (calgranulin B), part of a complex (27e10 antigen) with S100A8 that activates beta2 integrin (ITGB2) ligand binding, thereby mediating neutrophil adhesion during inflammation, binds and transports fatty acids | −5.4 |
| KCNG2 | Potassium voltage channel subfamily gamma 2, a member of the Kv6 family of ion channels, functions as a votage-gated potassium channel upon interaction with Kv2.1 alpha subunit, may contribute to cardiac action potentiation repolarization | −5.5x |
| FABP1 | Fatty acid binding protein 1 liver, positive regulator of peroxisome proliferator activated receptor alpha (PPARA), plays a role in fatty acid transport, cell proliferation, and apoptosis, increased expression is associated with prostate cancer | −7.2 |

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention is claimed as follows:

1. A method for predicting whether a tyrosine kinase inhibitor is toxic to one or more cardiomyocytes, said method comprising:
 (a.) treating the one or more cardiomyocytes with the tyrosine kinase inhibitor; and
 (b.) measuring a level of lipids in the one or more cardiomyocytes treated with the tyrosine kinase inhibitor,
whereby the tyrosine kinase inhibitor is predicted to be toxic to the one or more cardiomyocytes where the level of lipids in the one or more cardiomyocytes increases upon treatment with the tyrosine kinase inhibitor as compared to cardiomyocytes not treated with the tyrosine kinase inhibitor.

2. The method of claim 1, wherein the tyrosine kinase inhibitor is a dual tyrosine kinase inhibitor.

3. The method of claim 2, wherein the tyrosine kinase inhibitor is an erbB inhibitor.

4. The method of claim 2, wherein the tyrosine kinase inhibitor is an antibody.

5. The method of claim 4, wherein the antibody is trastuzumab.

6. The method of claim 2, wherein the tyrosine kinase inhibitor is a small molecule inhibitor.

7. The method of claim 6, wherein the small molecule inhibitor is GW572016 or GW2974.

8. The method of claim 1, wherein the lipids are selected from the group consisting of a triglyceride and a cholesterol.

9. A method for predicting cardiac toxicity in response to treatment with a tyrosine kinase inhibitor, said method comprising:
 (a.) treating one or more cardiomyocytes with the tyrosine kinase inhibitor; and
 (b.) measuring a level of lipids in the one or more cardiomyocytes treated with the tyrosine kinase inhibitor,
whereby a patient is predicted to exhibit cardiac toxicity in response to treatment with the tyrosine kinase inhibitor where the level of lipids in the one or more cardiomyocytes increases upon treatment with the tyrosine kinase inhibitor as compared to cardiomyocytes not treated with the tyrosine kinase inhibitor.

10. The method of claim 9, wherein the tyrosine kinase inhibitor is a dual tyrosine kinase inhibitor.

11. The method of claim 10, wherein the tyrosine kinase inhibitor is an erbB inhibitor.

12. The method of claim 10, wherein the tyrosine kinase inhibitor is an antibody.

13. The method of claim 12, wherein the antibody is trastuzumab.

14. The method of claim 10, wherein the tyrosine kinase inhibitor is a small molecule inhibitor.

15. The method of claim 14, wherein the small molecule inhibitor is GW572016 or GW2974.

16. The method of claim 9, wherein the lipids are selected from the group consisting of a triglyceride and a cholesterol.

17. The method of claim 1, wherein the one or more cardiomyocytes are from a population of cardiomyocytes and whereby the tyrosine kinase inhibitor is predicted to be toxic to the population of cardiomyocytes where the level of lipids in the one or more cardiomyocytes increases upon treatment with the tyrosine kinase inhibitor as compared to cardiomyocytes not treated with the tyrosine kinase inhibitor.

* * * * *